US012788844B2

(12) United States Patent
Shashkov et al.

(10) Patent No.: US 12,788,844 B2
(45) Date of Patent: Nov. 10, 2026

(54) IMPLANT WITH CERAMIC COATING, METHOD OF FORMING AN IMPLANT, AND METHOD OF APPLYING A CERAMIC COATING

(71) Applicant: BIOCERA MEDICAL LIMITED, England (GB)

(72) Inventors: Pavel Shashkov, Linton (GB); Aleksey Yerokhin, Worsley (GB); Sergey Usov, Cambridge (GB)

(73) Assignee: BIOCERA MEDICAL LIMITED, Haverhill (GB)

( * ) Notice: Subject to any disclaimer, the term of this patent is extended or adjusted under 35 U.S.C. 154(b) by 1533 days.

(21) Appl. No.: 17/273,088

(22) PCT Filed: Sep. 4, 2019

(86) PCT No.: PCT/GB2019/052467
§ 371 (c)(1),
(2) Date: Mar. 3, 2021

(87) PCT Pub. No.: WO2020/049299
PCT Pub. Date: Mar. 12, 2020

(65) Prior Publication Data
US 2021/0338889 A1 Nov. 4, 2021

(30) Foreign Application Priority Data
Sep. 4, 2018 (GB) ..................................... 1814353

(51) Int. Cl.
*A61L 27/32* (2006.01)
*A61L 27/04* (2006.01)
*A61L 27/06* (2006.01)
*A61L 27/10* (2006.01)
*A61L 27/54* (2006.01)
*A61L 27/56* (2006.01)

(52) U.S. Cl.
CPC ............. *A61L 27/32* (2013.01); *A61L 27/047* (2013.01); *A61L 27/06* (2013.01); *A61L 27/10* (2013.01); *A61L 27/54* (2013.01); *A61L 27/56* (2013.01); *A61L 2300/406* (2013.01); *A61L 2300/41* (2013.01); *A61L 2300/414* (2013.01); *A61L 2300/606* (2013.01); *A61L 2420/02* (2013.01); *A61L 2420/06* (2013.01); *A61L 2420/08* (2013.01); *A61L 2430/02* (2013.01)

(58) Field of Classification Search
CPC ........ A61L 27/32; A61L 27/047; A61L 27/06; A61L 27/10; A61L 27/54; A61L 27/56; A61L 2300/406; A61L 2300/41; A61L 2300/414; A61L 2420/02; A61L 2420/06; A61L 2420/08; A61L 2430/02; A61L 27/50; A61L 2300/606
See application file for complete search history.

(56) References Cited

U.S. PATENT DOCUMENTS

| | | | | |
|---|---|---|---|---|
| 2004/0158330 A1 | 8/2004 | Miller et al. | | |
| 2010/0131062 A1* | 5/2010 | Andersson | A61L 27/50 | 427/2.27 |
| 2012/0276336 A1* | 11/2012 | Malshe | A61L 27/32 | 428/206 |
| 2017/0001920 A1 | 1/2017 | Berner | | |

FOREIGN PATENT DOCUMENTS

| | | |
|---|---|---|
| EP | 1696816 | 9/2006 |
| EP | 2077124 | 7/2009 |
| GB | 2521621 | 7/2015 |
| WO | 03/039609 | 5/2003 |
| WO | 2012/107754 | 8/2012 |

OTHER PUBLICATIONS

Office Action issued for European Patent Application No. 19766317. 2, Feb. 21, 2023, 26 pages.
Takao Hanawa, "Biofunctionalization of titanium for dental implant," Japanese Dental Science Review (2010) 46, pp. 93-101.
Bartáková S. et al., "New Titanium Beta-Alloys for Dental Implantology and their laboratory based assays of biocompatibility," Scripta Medica, vol. 82, No. 2 (2009) pp. 76-82.
Maureen E. Kelleher et al., "Use of Silver Sodium Zirconium Phosphate Polyurethane Foam Wound Dressing on Wounds of the Distal Forelimb," AAEP Proceedings vol. 59 (2013), p. 489.
R. K. Choudhary, et al., "Structural and optical properties of anodic orthorhombic zirconia films," Surface Engineering, vol. 34, No. 9 (2018), pp. 655-659, DOI: 10.1080/02670844.2017.1320033.
Gilles Trolliard et al., "Martensitic phase transition in pure zirconia: a crystal chemistry viewpoint," Oldenbourg Wissenschaftsverlag, (2011), pp. 264-290.
H.C. Choe, "Nanotubular surface and morphology of Ti-binary and Ti-ternary alloys for biocompatibility," Thin Solid Films 519 (2011), pp. 4652-4657.
Kaluderovic M. et al., "First titanium dental implants with white surfaces: Preparation and in vitro tests," Dental materials 30 (2014), pp. 759-768.

(Continued)

*Primary Examiner* — Snigdha Maewall
(74) *Attorney, Agent, or Firm* — HSML P.C.

(57) ABSTRACT

An implant comprises a metal body having a ceramic coating comprising monoclinic and orthorhombic phases of zirconium oxide ZrO2 and at least one multi-metal phosphate from the group comprising I-IV metal phosphates. A method of forming an implant is provided. A method of applying a ceramic coating to a metal body comprises the step of electrochemical oxidation of at least a portion of the surface of a metal body in aqueous electrolyte; in which the electrolyte contains at least two elements from a group consisting of zirconium, titanium, magnesium, phosphorus, calcium, fluoride, potassium, sodium, strontium, sulphur, argentum, zinc, copper, silicon, gallium; in which electrochemical oxidation is conducted in a plasma discharge (PEO) mode for at least one interval of time, and non-discharge modes for at least two intervals of time.

21 Claims, 5 Drawing Sheets

(56) References Cited

OTHER PUBLICATIONS

H. Hu et al., "Antibacterial activity and increased bone marrow stem cell functions of Zn-incorporated TiO2 coatings on titanium," Acta Biomaterialia 8 (2012) pp. 904-915.
An Zhang et al., "The dual function of Cu-doped TiO2 coatings on titanium for application in percutaneous implants," Journal of Materials Chemistry B, Jun. 7, 2016, Issue 21, Royal Society of Chemistry, pp. 3623-3844.
Kuan-Chen Kung et al., "Bioactivity and corrosion properties of novel coatings containing strontium by micro-arc oxidation," Journal of alloys and compounds, 508 (2010), pp. 384-390.
Jinsong Liu et al., "Gallium and silicon synergistically promote osseointegration of dental implant in patients with osteoporosis,"Medical Hypotheses 103 (2017) pp. 35-38.
Young-Taeg Sul et al., "Oxidized bioactive implants are rapidly and strongly integrated in bone. Part I—experimental Implants," Clin. Oral Impl. Res. 17 (2006), pp. 521-526.
Le Guehennec et al., "Surface treatments of titanium dental implants for rapid osseointegration," Dental materials 23 (2007), pp. 844-854.
W.-H. Song et al., "Biomimetic apatite coatings on micro-arc oxidized titania," Biomaterials 25 (2004), pp. 3341-3349.
B.D. Cullity et al., Elements of X-Ray Diffraction, 3rd Ed., Prentice- Hall Inc. (2001), 8 pages.
Zhongping Yao et al., "Effect of Na2SO4 on Structure and Corrosion Resistance of Ceramics Coatings Containing Zirconium Oxide on Ti—6Al—4V Alloy," Journal of the American Ceramic Society, vol. 89, No. 9, 2006, pp. 2929-2932.
Jerome Chevalier et al., "The Tetragonal-Monoclinic Transformation in Zirconia: Lessons Learned and Future Trends," Journal of the American Ceramic Society, vol. 92, No. 9, 2009, pp. 1901-1920.
G. Trolliard et al., "Pure orthorhombic zirconia islands grown on single-crystal sapphire substrates," Acta Materialia, Elsevier, Oxford, GB, vol. 55, 2007, pp. 6011-6018.
Gowtham et al., "An investigation on ZrO2 nano-particle incorporation, surface properties and electrochemical corrosion behaviour of PEO coating formed on Cp-Ti," Surface and Coatings Technology, vol. 313, 2017, pp. 263-273.
Rudnev et al., "Plasma-Electrolytic Oxidation of Titanium in Zr(SO4)2-Containing Electrolyte," Protection of Metal and Physical Chemistry of Surfaces, vol. 46, No. 6, 2010, pp. 704-709.
Shokouhfar M. et al., "Preparation of ceramic coating on Ti substrate by plasma electrolytic oxidation in different electrolytes and evaluation of its corrosion resistance: Part II," Applied Surface Science, 258, No. 7, 2012, pp. 2416-2423.
International Search Report and Written Opinion issued for PCT/GB2019/052467, Jan. 30, 2020, 23 pages.
Search Report issued for Application No. GB 1814353.7, May 23, 2019, 5 pages.

* cited by examiner

IMPLANT WITH CERAMIC COATING, METHOD OF FORMING AN IMPLANT, AND METHOD OF APPLYING A CERAMIC COATING

TECHNICAL FIELD

The invention relates to metal implants with ceramic surface coatings, to methods of forming an implant, and to methods of applying a ceramic coating to a metal body.

BACKGROUND

Metal implants are known to benefit from coatings applied on their surface to enhance their biocompatibility, osseointegration and prevent the implant metal release into tissue (Takao Hanawa, Biofunctionalization of titanium for dental implant, Japanese Dental Science Review (2010) 46, 93-101). Different metals such as titanium (Ti), zirconium (Zr), tantalum (Ta), iron (Fe) and magnesium (Mg) and their alloys are used for medical implants. The most popular material is titanium (Ti) and its alloys, thanks to their biocompatibility.

Ti Grade 5 (Ti-6Al-4V) alloy is a preferred material for implant applications due to its high mechanical strength and toughness. Ti grade 5 alloy contains 4 wt % of vanadium and 6 wt % of aluminium both being considered not biocompatible (Bartáková S. et al, New Titanium Alloys for Dental Implantology and their laboratory based assays of biocompatibility, Scripta Medica, Volume 82, No. 2, 2009, 76-82). Metal implants are associated with migration of metallic elements in peri-implant tissue. Significant amounts of elements present in the Ti alloy were found in various organs such as lungs, liver, spleen and kidneys (Schliephake H, Reiss J, Urban R, et al. Freisetzung von Titan aus Schraubenimplantaten. Z Zahnärztllmplantol. 1991; 7:6-10.7). This may lead to serious health problems because, e.g. vanadium ions have been found to cause cytotoxic effects and adverse tissue reactions, while aluminium ions have been associated with neurological disorders (H. C. Choe, Nanotubular surface and morphology of Ti-binary and Ti-ternary alloys for biocompatibility, Thin Solid Films 519 (2011) 4652-4657).

The colour of the implant surface is an important aesthetic factor especially for dental implants. The dark grey colour of Ti dental implants can make them visible when the soft peri-implant mucosa is of thin biotype or recedes over time. The preferred colour for a dental implant is the colour of tooth or bone which is commonly classified as white or ivory. Although the colour of teeth or bones exhibits some variability, within the framework of this application it shall be referred to as white.

A popular method of biofunctionalisation of implant surface is the deposition or calcium phosphate, commonly in the form of hydroxyapatite (HA). WO 03/039609 A1 proposes the electrophoretic coating of implants with hydroxyapatite as a bioactive surface material. HA is known to promote osseointegration but does not provide properties of a strong physical barrier. In the course of implant integration, HA is gradually substituted by natural bone which then comes into direct contact with the metal.

Alternative method for applying biocompatible coating on Ti dental implants which exhibits insulating properties is surface oxidation by anodising or plasma electrolytic oxidation (PEO) which is also called microarc oxidation (MAO) or spark anodising. Oxidation of titanium implant material forms a layer of titanium dioxide ($TiO_2$) on its surface.

EP 1696816 A1 by NobelBiocare discloses Ti implant with a $TiO_2$ coating which has a porous surface structure. NobelBiocare coating is a phosphate-enriched crystalline titanium oxide produced by Microarc Oxidation. NobelBiocare surface has a dark grey colour which does not have aesthetic advantages.

EP2077124 describes Ti implant with a biocompatible surface coating produced by PEO that contains oxide of titanium and oxide of zirconium. This was achieved by using an aqueous electrolyte containing a dissolved salt of zirconium sulphate. Zr ions are incorporated in the surface during oxidation of Ti alloy forming complex titania-zirconia oxides [4]. This coating is claimed to have only monoclinic zirconium oxide crystalline phase and no other high-temperature forms of zirconium oxide. Such coating has white colour only on commercially pure Ti but on the most widely used Ti alloy of Grade 5, its colour is grey.

PEO treatments or anodising of Grade 5 Ti alloys result in oxide coatings of grey colour due to presence of vanadium in the alloy that provides dark grey shade to the resulting oxide. PEO coatings on Ti are highly porous throughout the coating thickness which is claimed to enhance osseointegration. But such a high porosity compromises the coating barrier properties, reducing its ability to prevent implant metal leaching into peri-implant tissue.

WO2012/107754 describes a process of non-spark electro-chemical oxidation (ECO) in colloidal electrolytes different from traditional anodising or PEO. ECO provides a smooth and dense ceramic layer with high insulating properties. It can be advantageous for metal implants providing their insulation from tissue. Although this method does not provide a highly convoluted surface required to enhance implant osseointegration.

It is the aim of this invention to provide a metal implant with multifunctional ceramic coating with a combination of properties such as (1) enhanced biocompatibility and osseointegration, (2) a physical barrier preventing migration of metal ions and (3) a bone-like colour.

SUMMARY OF THE INVENTION

The invention provides, in various aspects, an implant comprising a metal body having a ceramic coating, a method of forming an implant, and a method of applying a ceramic coating to a metal body, as defined in the appended independent claims to which references should be made. Preferred or advantageous features of the invention are set out in various dependent sub-claims.

In the first aspect, the invention may provide an implant comprising a metal body having a ceramic coating with a desired combination of properties.

The first aspect may provide an implant comprising a metal body having a ceramic coating, in which the ceramic coating material contains monoclinic and orthorhombic phases of zirconium oxide $ZrO_2$, and at least one multi-metal phosphate from the group of I-IV metal phosphates.

The ceramic coating may be formed at least in part by multi-stage electrochemical oxidation of at least a portion of the metal body.

Coatings formed by electrochemical oxidation have distinctive features and advantages compared to those formed by plasma spraying or electrodeposition commonly used for surfacing of metal implants. Those advantages include excellent adhesion to the metal substrate because the oxide coating is a result of conversion of the substrate itself into the oxide rather than a deposition of ceramic material to a surface of a dissimilar metallic material.

Coatings formed by electrochemical oxidation are characterised by a controllable morphology and porosity which can be adjusted for different requirements. Control of ceramic coating properties is conducted through a control of electrical parameters of the process and composition of electrolyte.

A control over the process power density according to the identified rule enables a desired three layered structure to be formed on the surface.

The ceramic coating material may contain monoclinic and orthorhombic phases of zirconium oxide $ZrO_2$.

Monoclinic and orthorhombic phases of zirconium oxide $ZrO_2$ are advantageously formed by the high-energy electrochemical oxidation process used to form the ceramic coating on the metal implant body.

Zirconium may be present as zirconium oxide $ZrO_2$ in the ceramic coating because the metal body itself comprises zirconium, and/or because the electrolyte used during electrochemical oxidation contains zirconium or zirconium oxide that is incorporated into the ceramic coating during oxidation.

The inventors have found that the zirconium oxide content of the ceramic coating is beneficial for the implant because $ZrO_2$ is advantageously biocompatible, and the presence of the orthorhombic phase is beneficial for enhancement of the structural integrity of the ceramic coating thanks to its ability to undergo a stress induced phase transformation utilised for toughening of zirconia ceramics.

The ceramic coating material may comprise at least one multi-metal phosphate from the group comprising or consisting of I-IV metal phosphates. The ceramic coating material may comprise at least one I-IV multi-metal phosphate.

In order to form an I-IV multi-metal phosphate in the ceramic coating during electrochemical oxidation, at least one group I metal and at least one group IV metal are present in the metal body or the electrolyte, and phosphorus and oxygen are present in the electrolyte used during oxidation. During the electrochemical oxidation of the metal body and growth of the ceramic coating, the groups I and IV metals react with the phosphorus and oxygen to form a multimetal-phosphate in the ceramic coating.

The inventors have found that a multi-metal phosphate is a beneficial component of an implant coating, because it contains orthophosphate groups $PO_4^{3-}$ beneficial for calcium phosphate induction on the surface, which enhances surface bioactivity.

The group I metal is preferably potassium and/or sodium. The group I metal is preferably provided in the electrolyte used for oxidation, and incorporated into the ceramic coating during oxidation.

The group IV metal is preferably titanium or zirconium. The group IV metal may be present in the metal body before oxidation. Alternatively, or additionally, the group IV metal may be provided in the electrolyte used for oxidation, and incorporated into the ceramic coating during oxidation.

The ceramic coating may comprise a plurality of layers.

The ceramic coating may comprise a top surface layer with a roughness Ra greater than 0.4 micrometres. The ceramic coating may comprise a bone-coloured top surface layer.

The ceramic coating may comprise a barrier layer at the interface with the metal body.

The ceramic coating may comprise an intermediate layer between a surface layer and a barrier layer. The intermediate layer may be a scratch-resistant layer.

In a preferred embodiment the ceramic coating may comprise three layers, including:

- a top surface layer, preferably with a roughness Ra greater than 0.4 micrometres,
- an intermediate layer, and
- a barrier layer at the interface with the metal body.

In preferred embodiments, the top layer may provide a bone like colour and convoluted surface morphology with roughness Ra in the range between 0.4 and 2 micrometres, which is beneficial for osseointegration. A bone-like colour may occur in a ceramic with CIELAB colour space values of L* from 65 to 80, a* from −3 to +3 and b* from −2 to +5 and reflectance in the visible wavelength range above 30%.

The intermediate, or middle, layer may be characterised by high hardness and scratch resistance and supports structural integrity of the coating.

The bottom layer situated at the interface with the metal may be dense and serves as a barrier to metal ion migration into the peri-implant tissue.

The total thickness of the ceramic layer may be between 5 and 40 micrometres. Layers thinner than 5 micrometre do not allow formation of the beneficial three layered structure. Layers thicker than 40 micrometres are difficult to apply electrochemically due to their high electrical resistance which is proportional to the layer thickness.

The ceramic coating may have a thickness of between 5 micrometres and 40 micrometres, preferably between 7 micrometres and 30 micrometres, particularly preferably between 10 micrometres and 40 micrometres.

Where the ceramic coating comprises multiple layers, the top layer of the ceramic coating preferably has a thickness of between 2 micrometres and 15 micrometres, preferably between 3 micrometres and 10 micrometres.

The intermediate layer preferably has a thickness of between 2 micrometres and 20 micrometres, preferably between 5 micrometres and 15 micrometres.

The barrier layer preferably has a thickness of between 1 micrometre and 7 micrometres, preferably between 2 micrometres and 5 micrometres.

The surface layer of the ceramic coating may have a porosity of greater than 25%, for example between 25% and 40% porosity.

The intermediate layer of the ceramic coating may have a porosity of between 5% and 15%. Thus, the intermediate layer may be relatively more dense than the surface layer.

The barrier layer of the ceramic coating may have a porosity below 5%, for example between 1% and 5% porosity. Thus, the barrier layer may be relatively more dense than both the intermediate layer and the surface layer.

Coating porosity may be determined by image analysis of cross-section SEM micrographs using ImageJ software.

Scratch resistance of the coating was evaluated by VTT scratch tester with diamond indenter having tip curvature radius of 200 micrometres with increasing load over 15 mm distance. Indenter reached the substrate at a critical load in the range of 10-18 N which is a higher value compared to that measured anodic oxide films (5-8N) or galvanically deposited HA (4-7N). Around 80% of the distance before the perforation the indenter ploughs through the middle layer 2 which constitutes only 50% of the coating thickness. This demonstrated that a high scratch resistance of the coating is provided predominantly by the intermediate layer of ceramic material. Scratch resistance is beneficial for metal implants because it protects surface integrity during implant installation and exploitation. It prevents creation of exposed metal areas which cause ion leaching. That is particularly important for titanium which does not provide wear resistance and is prone to fretting.

The ceramic coating material may present a complex of nanocrystalline oxides, incorporating oxides of the implant metal body, zirconium oxide, multi-metal phosphate from the group comprising I-IV metal phosphates, e.g. alkali-metal zirconium phosphates and alkali-metal titanium phosphates, and other compounds that could be in either crystalline or amorphous form.

The alkali-metal zirconium phosphate can be potassium zirconium phosphate of kosnarite type $KZr_2(PO_4)_3$, sodium zirconium phosphate $NaZr_2(PO_4)_3$ or silver sodium zirconium phosphate $AgNaZr(PO_4)_2$. The alkali-metal titanium phosphate can be sodium titanium phosphate $NaTi_2(PO_4)_3$ or potassium titanil phosphate $KTiOPO_4$.

The bone-like colour of the ceramic coating is primarily provided by the presence of zirconium oxide $ZrO_2$, alkali-metal titanium phosphate or alkali-metal zirconium phosphate, for example kosnarite $KZr_2(PO_4)_3$.

Colour of developed ceramic surfaces evaluated by Datacolor 660 spectroscope provided values in CIELAB colour space in the ranges of L*=65 . . . 80, a*=−3 . . . +3 and b*=−2 . . . +5. The low values of a* and b* indicate a well balanced combination between red-green and yellow-blue colours, whereas high values of lightness L* indicate a close to white light-grey shade of the surface.

Optical reflectance of ceramic surface were measured by a spectrophotometer CM 2600 (Konica Minolta) in the visible wavelength range. Reflectance of teeth according to VITA Zahnfabric ranges in the interval between 30% and 70%. Mean reflectance values for Ti alloy implants with etched surface and anodised implants laid in the range of 22-29% while produced implants with ceramic coating had reflectance in the range 30-45%.

Zirconium oxide is known to possess biocompatible properties (Kaluderovic M. et al, First titanium dental implants with white surfaces: Preparation and in vitro tests, Dental materials, 30 (2014) 759-768).

The multi-metal phosphate contains orthophosphate groups $PO_4^{3-}$ beneficial for calcium phosphate induction on the surface, which enhances surface bioactivity.

Zirconium oxide is present in the coating in two dominant phases—monoclinic and orthorhombic. A presence of the orthorhombic phase is beneficial for enhancement of the structural integrity within the surface layer thanks to its ability to undergo a stress induced phase transformation utilised for toughening of zirconia ceramics.

Other elements can be present in the ceramic matrix to enhance its bioactive or antibacterial properties. Those elements are from the group comprising calcium, magnesium, titanium, potassium, sodium, phosphorus, fluorine, sulphur, silver, zinc, copper, strontium, silicon.

The inventors have found that the presence of calcium, phosphorus, fluorine, sodium and magnesium promotes the biocompatibility of oxide material, making it more suitable for use as an implant coating.

Antibacterial properties are known to be provided by silver, zinc (H. Hu, W. Zhang, Y. Qiao, X. Jiang, X. Liu, C. Ding, Antibacterial activity and increased bone marrow stem cell functions of Zn-incorporated TiO2 coatings on titanium, Acta Biomaterialia 8 (2012) 904-915), copper (Lan Zhang, Jiaqi Guo, Xiaoyan Huang, Yanni Zhang and Yong Han, The dual function of Cu-doped TiO2 coatings on titanium for application in percutaneous implants, Journal of Materials Chemistry, 7 Jun. 2016, Issue 21, p 3623-3844), strontium (Kuan-Chen Kung et al, Bioactivity and corrosion properties of novel coatings containing strontium by micro-arc oxidation, Journal of alloys and compounds, 508 (2010),384-390), gallium (Gallium and silicon synergistically promote osseointegration of dental implant in patients with osteoporosis, Liu J et al Medical Hypotheses 103 (2017) 35-38) sulphur and silicon (Young-Taeg Sul, Yongsoo Jeong, Carina Johansson, Tomas Albrektsson, Oxidized bioactive implants are rapidly and strongly integrated in bone. 7 Jul. 2007 https://doi.org/10.1111/j.1600-0501.2005.01230.x). They provide a balance between antibacterial effectiveness and cytotoxicity.

The elementary signature of the ceramic material may be provided by zirconium, phosphorus, oxygen, a base metal of the implant and at least one of the elements from the group: calcium, magnesium, titanium, potassium, sodium, fluorine, sulphur, silver, zinc, copper, strontium, silicon, gallium.

In a preferred embodiment, the elementary signature of the ceramic material is provided by zirconium, potassium, phosphorus, oxygen and a base metal of the implant and contains at least one of the elements from the group: calcium, magnesium, titanium, potassium, sodium, fluorine, sulphur, silver, zinc, copper, strontium, silicon.

Preferably the ceramic coating material contains at least four, or at least five, elements from the group consisting of: zirconium, titanium, magnesium, oxygen, phosphorus, calcium, fluoride, potassium, sodium, strontium, sulphur, argentum, zinc, copper, silicon.

The ceramic coating material may contain at least four, or at least five, elements from the group consisting of: zirconium, titanium, magnesium, oxygen, phosphorus, calcium, fluoride, potassium, sodium, strontium, sulphur, argentum, zinc, copper, silicon, gallium.

The invention may provide a metal substrate with ceramic coating that has nanocrystalline structure. The developed nanocrystalline ceramic material may be formed by equiaxed grains with average size varied between 20 and 100 nanometres. This may advantageously prevent excessive brittleness of the ceramic layer and provides ability to cover complex shapes. The nanocrystalline structure of ceramic was provided by the use of short forming electrical pulses in the electrochemical process. To achieve the nanocrystalline structure, the pulse duration was shorter than one millisecond and the repetition frequency was above 1 kHz.

The surface of the ceramic coating may have a roughness Ra of greater than or equal to 0.4 μm, or 0.5 μm, or 0.6 μm, and less than or equal to 1.2 μm, or 1.5 μm, or 2 μm.

Surface roughness may be measured using a Veeco Dektak 150 Surface Profiler.

The invention may provide an implant in which the metal body comprises one of the following metals: titanium, zirconium, magnesium, tantalum or an alloy or intermetallic compound of any of the above metals. These materials are suitable for the developed multi-stage electrochemical processing resulting oxide films which serve as a matrix for incorporation of colloidal particles and forming of complex multifunctional oxide ceramic coating with desired properties.

In a preferred embodiment the metal body of the implant may comprise a titanium alloy.

Particularly preferably the metal body may comprise, or consist of, Ti Grade 5 (Ti-6Al-4V) alloy.

The invention may provide a ceramic surface of an implant according to the previous aspects which is impregnated or top coated with an additional substance material which enhances osseointegration and biocompatibility. Those materials can be anti-inflammatory drugs, antibiotics, hydroxyapatite, fluoride, various bone stimulating agents, including bisphosphonates; bioactive lipids such as lysophosphatidic acids; osteogenic growth factors such as bone morphogenetic proteins (BMPs).

The ceramic surface of the implant may be impregnated or top coated with a material such as bone healing enhancement drugs, or cancer treatment materials such as P32 isotope or caesium chloride.

Highly developed surface ceramic top layer serves as a reservoir for those materials and enables their gradual release. This may allow controlled prolonged drug delivery. The materials can be applied by any conventional method including dipping, spraying, galvanic deposition, sol-gel techniques, vacuum deposition and others.

The implant may be, for example, a dental implant, or a medical implant. The implant may be an implant for human and/or animal applications.

A dental implant with a nanoceramic layer impregnated with bone stimulating agent offers a possibility for implant immediate implantation after tooth extraction rather than after regeneration of the bone using a membrane or bone replacement material.

In a further aspect, the invention may provide a method of applying a ceramic coating to a metal body which comprises one or more of the following main steps:

- Step I: manufacturing of the metal implant body by forging, casting, thixomolding, machining, turning, milling, additive manufacturing (e.g. 3D printing), CVD deposition, wire erosion and spark erosion;
- Step II: Metal implant surface preparation by polishing, blasting, etching and/or cleaning;
- Step III: Surface electrochemical oxidation of at least a part of the metal body surface in a colloidal electrolyte.

The first and second steps are optional, and may be implemented via conventional manufacturing techniques.

The third step is novel and presents an inventive step in electrochemical coating.

A method of applying a ceramic coating to a metal body may comprise the step of electrochemical oxidation of at least a portion of the surface of a metal body in aqueous electrolyte; in which the electrolyte contains at least two elements from a group consisting of zirconium, titanium, magnesium, phosphorus, calcium, fluoride, potassium, sodium, strontium, sulphur, argentum, zinc, copper, silicon.

The electrolyte may contain at least two elements from a group consisting of zirconium, titanium, magnesium, phosphorus, calcium, fluoride, potassium, sodium, strontium, sulphur, argentum, zinc, copper, silicon, gallium.

The electrolyte preferably contains zirconium, phosphorus and an alkali-metal, which is preferably potassium or sodium.

The electrolyte may be an aqueous colloidal solution comprising zirconium oxide $ZrO_2$ powder or nano-powder.

The method of applying a ceramic coating to a metal body may be a method of manufacturing an implant.

The method may produce a coated metal body for use as an implant.

Electrochemical oxidation may be conducted in a plasma discharge (PEO) mode for at least one interval of time, and non-discharge modes for at least two intervals of time.

The energy density of the electrochemical oxidation process preferably exceeds the value of 20 $kW/dm^2$ during oxidation of the metal body. This high energy density of the electrochemical oxidation may advantageously promote the formation of the monoclinic and orthorhombic phases of zirconium oxide in the coating, as well as promoting formation of multi-metal phosphate in the coating.

The energy density of the electrochemical oxidation process may exceed the value of 20 $kW/dm^2$ for an interval of time of at least 1 minute.

Electrochemical oxidation of the metal body is conducted in an electrolytic reactor or tank containing an aqueous, or water-based, electrolyte. At least a portion the surface of the implant on which it is desired to form the coating is in contact with the electrolyte.

The method may comprise electrically biasing the implant with respect to the electrode by applying a sequence of voltage pulses of alternating polarity.

The use of high energy pulses may advantageously ensure integration of colloidal particles from the electrolyte into the oxide of the metal body in the course of oxidation.

In a preferred embodiment of the method, the pulse duration is less than one millisecond and the repetition frequency is above 1 kHz. This may advantageously lead to formation of a nanocrystalline ceramic coating structure, which preferably has an average crystal size of less than 100 nm.

It is advantageous that electrochemical process is controlled in a way that forms a coating that includes three layers:

- The top layer provides a bone like colour and convoluted surface morphology with roughness Ra in the range greater than 0.4 micrometres, preferably between 0.4 and 2 micrometres, which is beneficial for osseointegration;
- the intermediate layer is characterised by high hardness and scratch resistance and supports mechanical integrity of the coating; and
- the bottom layer situated at the interface with the metal is dense and serves as a barrier to metal ion migration into the peri-implant tissue.

The desired structure of the coating is achieved through a control of energy density of the electrochemical process during different stages of the process. The energy density is defined here as an amount of electrical energy (W) flowing per a unit of material surface (S). Its value equals to a value of (electrical current through the electrolyte)×(applied voltage)/(coated surface) and it is measured in $W/dm^2$.

Electrochemical oxidation may be conducted in a plasma discharge (PEO) mode for at least one interval of time, and non-discharge modes for at least two intervals of time.

The energy density of the electrochemical oxidation process may exceed the value of 20 $kW/dm^2$ for an interval of time of at least 1 minute. The energy density of the electrochemical oxidation process may exceed the value of 20 $kW/dm^2$ for an interval of time of between 1 and 20 minutes, or between 5 and 15 minutes, or between 8 and 12 minutes.

The process of electrochemical oxidation may comprise the following consecutive steps:

a) pre-discharge energy ramping step,
b) plasma electrolytic oxidation step in which the process energy density exceeds the value of 20 $kW/dm^2$,
c) post-discharge energy decrease step.

The method may comprise the additional fourth step of:

d) low energy quasi stationary step in which the process energy density does not exceed the value of 5 $kW/dm^2$.

At the first stage of the process, the applied energy is gradually increased from zero to a threshold value at which the first microarc discharge appears on the surface. That is achieved through an increase in the voltage amplitude of electric pulses. The first stage is a pre-discharge ramping stage. It has duration preferably between 0.1 and 2 min.

At the second stage, the energy density is increased above the discharge threshold value and the process can be classified as plasma electrolytic oxidation (PEO). Electrochemical oxidation in the PEO mode results in a rough surface of the ceramic coating due to multiple discharge events. The surface roughness can be controlled through a control of the applied energy and the duration of the PEO stage. The use of high energy pulses ensures integration of colloidal particles of electrolyte into the oxide of the substrate metal in the course of oxidation.

With gradual increase of energy density during the second stage it becomes higher than a point of zirconium oxide phase transformation, which leads for the formation of the orthorhombic phase of zirconium oxide. It was established that the formation of the orthorhombic $ZrO_2$ is achieved at energy densities exceeding 20 kW/dm$^2$. It corresponds to electrical pulse voltage amplitude above 400 Volts and electric current density above 50 A/dm2.

A combination of monoclinic and orthorhombic phases of zirconium oxide in this process is distinctly different from the phase composition of $ZrO_2$ component of the prior art EP2077124 coating, containing only monoclinic zirconia phase because the energy density in that process was insufficient to convert it to the orthorhombic phase.

At the end of second stage, the process energy is made to decrease by reduction of pulse voltage magnitude until the discharge phenomenon disappears. The PEO stage lasts preferably between 1 and 20 min. Durations shorter than 1 min do not provide sufficient effect for forming the required surface topography, wherein the desired surface roughness value is above Ra 0.4 micron.

The third stage is a post-discharge oxidation. The absence of discharge allows to form a more compact oxide ceramic material. Since the coating grows through oxidation of the substrate, this compact layer is positioned underneath the porous top layer formed during the PEO stage. The compact oxide layer has high toughness and scratch resistance that is beneficial for implant mechanical integrity. The third stage is characterised by a gradual decreasing of energy density. Duration of the third stage is preferably between 2 and 20 min.

The fourth stage of the process is characterised by maintaining the energy density at a relatively low quasi stationary level. During this period, the barrier layer at the interface with the metal is developed. This layer is characterised by low porosity and prevents leaching of substrate metal ions into the bone tissue through the ceramic coating. Duration of the fourth stage is preferably between 1 and 5 min.

Electrolytes used for coating different metals and alloys can differ but preferably include elements that provide coating with bone-like colour, biocompatibility and osseointegration. Those elements may include: zirconium, titanium, calcium, magnesium, potassium, sodium, phosphorus, fluorine, sulphur, silver, zinc, copper, strontium, silicon, gallium.

Presence of Ca, P, F, Na, Ga and Mg promotes biocompatibility of the oxide material.

Ag, Cu, Si, Sr, S and Zn are known to provide anti-inflammatory properties.

Desired surface colour is provided through the presence in ceramic layer of zirconium oxide and alkali-metal zirconium phosphate of kosnarite type. They are formed due to the presence of zirconium, phosphorus, potassium and sodium in electrolyte.

Elements are introduced in the ceramic coating during the electrochemical oxidation process as components of an aqueous electrolyte as ions and nanoparticles. The use of nanoparticles leads to the colloidal structure of the electrolyte.

Colour of coating can be enhanced through incorporation of oxides of titanium, magnesium or hydroxyapatite that all have white colour. Nanoparticles of those materials can be used for preparation of electrolytes together with nanoparticles of zirconium oxide.

Biocompatibility is known to be provided by magnesium oxide MgO, zirconium oxide $ZrO_2$ and titanium oxide $TiO_2$ (Le Guehennec et al, Surface treatments of titanium dental implants for rapid osseointegration, Dental materials 23 (2007) 844-854). Hydroxyapatite HA is known to enhance osseointegration (Song, W.-H.; Jun, Y.-K.; Han, Y.; Hong, S.-H., Biomimetic apatite coatings on micro-arc oxidized titania. Biomaterials 2004, 25, (17), 3341-3349). $ZrO_2$ has high hardness and its presence in ceramic matrix increases resistance to scratch and wear. Zirconium-alkali-earth phosphates are known to provide anti-bacterial effect (Maureen E. Kelleher et al, Use of Silver Sodium Zirconium Phosphate Polyurethane Foam Wound Dressing AAEP PROCEEDINGS Vol. 59 2013 489). Zirconium oxide, magnesium oxide, titanium oxide and hydroxyapatite can be introduced in electrolyte as nanoparticles.

Introduction of the elements in ionic form may be made through dissolving of their compounds in the aqueous electrolyte:

Zirconium is introduced through dissolving of zirconium sulphate or zirconium fluoride;

Potassium is introduced through dissolving of potassium fluoride, phosphate (preferably pyro- or orthophosphate) or hydroxide;

Sodium is introduced through dissolving of sodium fluoride, phosphate (preferably pyro- or orthophosphate) or hydroxide;

Phosphorus is introduced through dissolving of a phosphate salt or suspending fine HA particles in the electrolyte;

Calcium is introduced through dissolving of a calcium salt of straight-chain carboxylic acid, preferably acetate, propionate, lactate, gluconate, oxalate, citrate, glycerol phosphate; or suspending fine HA particles in the electrolyte;

Fluorine is introduced through dissolving of a fluoride salt;

Sulphur is introduced through dissolving of a sulphate salt;

Silver is introduced through dissolving of argentum sulphate;

Zinc is introduced through dissolving of zinc acetate;

Copper is introduced through dissolving of copper sulphate;

Strontium is introduced through dissolving of strontium fluoride;

Silicon is introduced through dissolving of sodium silicate;

Gallium is introduced through dissolving of gallium sulphate.

Thus to achieve desirable properties of the ceramic material, the electrolyte may contain zirconium, phosphorus and at least two of the elements from the group: potassium, sodium, calcium, magnesium, fluorine, sulphur, silver, zinc, copper, strontium or silicon.

In a preferred embodiment the electrolyte may contain zirconium, phosphorus and at least two of the elements from the group: potassium, sodium, calcium, magnesium, fluorine, sulphur, silver, zinc, copper, strontium, gallium or silicon.

The electrolyte may contain at least two, or at least three, or at least four elements from the group: zirconium, titanium, magnesium, phosphorus, calcium, fluoride, potassium, sodium, strontium, sulphur, argentum, zinc, copper or silicon.

In a preferred embodiment the electrolyte may contain at least two, or at least three, or at least four elements from the group: zirconium, titanium, magnesium, phosphorus, calcium, fluoride, potassium, sodium, strontium, sulphur, argentum, zinc, copper, gallium or silicon.

Features described above in relation to separate aspects of the invention may be applied to the other aspects of the invention.

According to a further aspect of the invention there may be provided a ceramic coating as defined in relation to the other aspects of the invention. There may be provided a ceramic coating, in which the ceramic coating comprises three layers, including a top surface layer with a roughness Ra greater than 0.4 micrometres, an intermediate layer, and a dense barrier layer at an interface with a metal body, in which the ceramic coating material contains monoclinic and orthorhombic phases of zirconium oxide $ZrO_2$, and at least one multi-metal phosphate from the group comprising I-IV metal phosphates.

According to a further aspect of the invention there may be provided a method of manufacturing an implant, comprising the step of: electrochemical oxidation of at least a portion of the surface of the metal body in aqueous electrolyte; in which the electrolyte contains at least two elements from a group consisting of zirconium, titanium, magnesium, phosphorus, calcium, fluoride, potassium, sodium, strontium, sulphur, argentum, zinc, copper, silicon, and optionally gallium; in which electrochemical oxidation is conducted in a plasma discharge (PEO) mode for at least one interval of time, and non-discharge modes for at least two intervals of time. The method of manufacturing an implant may comprise any of the further features defined herein in relation to the method of applying a ceramic coating to a metal body.

According to a further aspect of the invention there may be provided a method of forming an implant comprising a metal body having a ceramic coating, comprising the step of: electrochemical oxidation of at least a portion of the surface of a metal body in aqueous electrolyte, in which the metal body and/or the electrolyte contains zirconium, and in which the electrolyte contains phosphorus and at least one of sodium or potassium, such that the electrochemical oxidation forms a ceramic coating on the metal body, the ceramic coating containing monoclinic and orthorhombic phases of zirconium oxide $ZrO_2$, and at least one multi-metal phosphate from the group comprising I-IV metal phosphates.

Preferably the electrolyte contains at least two elements from a group consisting of zirconium, titanium, magnesium, phosphorus, calcium, fluoride, potassium, sodium, strontium, sulphur, argentum, zinc, copper, silicon.

The electrolyte may contain at least two elements from a group consisting of zirconium, titanium, magnesium, phosphorus, calcium, fluoride, potassium, sodium, strontium, sulphur, argentum, zinc, copper, silicon, and gallium.

Preferably electrochemical oxidation is conducted in a plasma discharge (PEO) mode for at least one interval of time, and non-discharge modes for at least two intervals of time.

Preferably the energy density of the electrochemical oxidation process exceeds the value of 20 $kW/dm^2$ during oxidation. Particularly preferably the energy density of the electrochemical oxidation process exceeds the value of 20 $kW/dm^2$ for an interval of time of at least 1 minute, or 2 minutes, or 5 minutes, or 10 minutes, or 20 minutes.

In a preferred embodiment the oxidation process comprises the step of electrically biasing the metal body with respect to the electrolyte by applying a sequence of voltage pulses of alternating polarity, during which the energy density of the electrochemical oxidation process exceeds the value of 20 $kW/dm^2$. This pulsed high-energy process may advantageously encourage the integration of colloidal particles from the electrolyte into the growing ceramic coating during oxidation, and lead to the formation of orthorhombic $ZrO_2$ and multi-metal phosphates with desirable properties.

Further features of the method of forming an implant may be as described above in relation to other aspects of the invention.

PREFERRED EMBODIMENTS OF THE INVENTION

Preferred embodiments of the invention will now be described with reference to the figures, in which.

Figure 1:
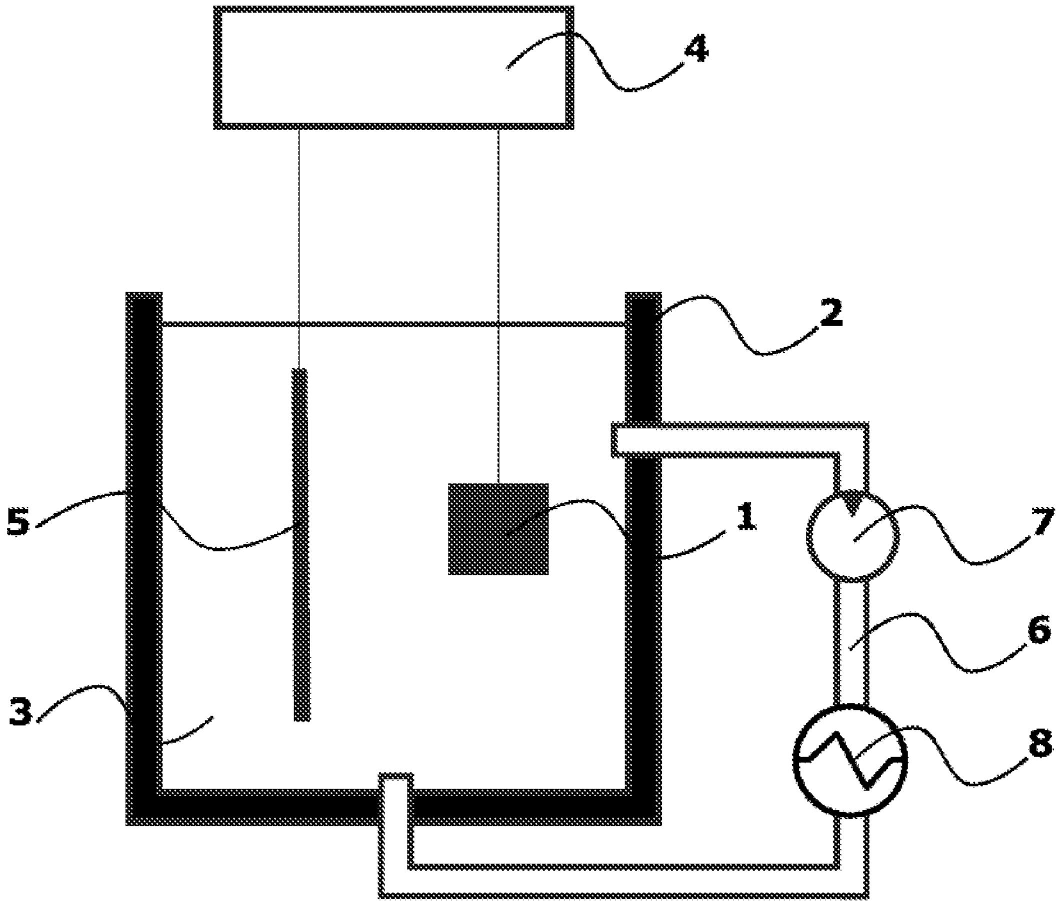
FIG. 1 is a schematic illustration of an electrolytic apparatus suitable to form a coating embodying the invention.

The implant 1 on which it is desired to form a ceramic coating is placed in a chemically inert tank 2, for example a tank formed from a polypropylene plastic, which contains an electrolyte solution 3. The electrolyte solution 3 is an aqueous solution, for example an aqueous solution of zirconium sulphate $Zr(SO_4)_2$, potassium pyrophosphate $K_4P_2O_7$ and potassium hydroxide KOH. The electrolyte may be a colloidal electrolyte comprising solid particles, for example zirconium oxide $ZrO_2$ nano powder.

The implant 1 is electrically connected to one output of a pulse power supply 4. An electrode 5, for example formed from stainless steel, is connected to a second output of the pulse power supply 4, and both the electrode 5 and the implant 1 are immersed in the electrolyte solution 3 contained within the tank 2. The pulse power supply 4 is capable of supplying electrical pulses of alternating polarity in order to electrically bias the implant 1 with respect to the electrode 5.

To control electrolyte temperature within optimal range between 20 and 25° C. the tank 2 is connected by tubes 6 with a pump 7 and a chiller 8.

Figure 2:
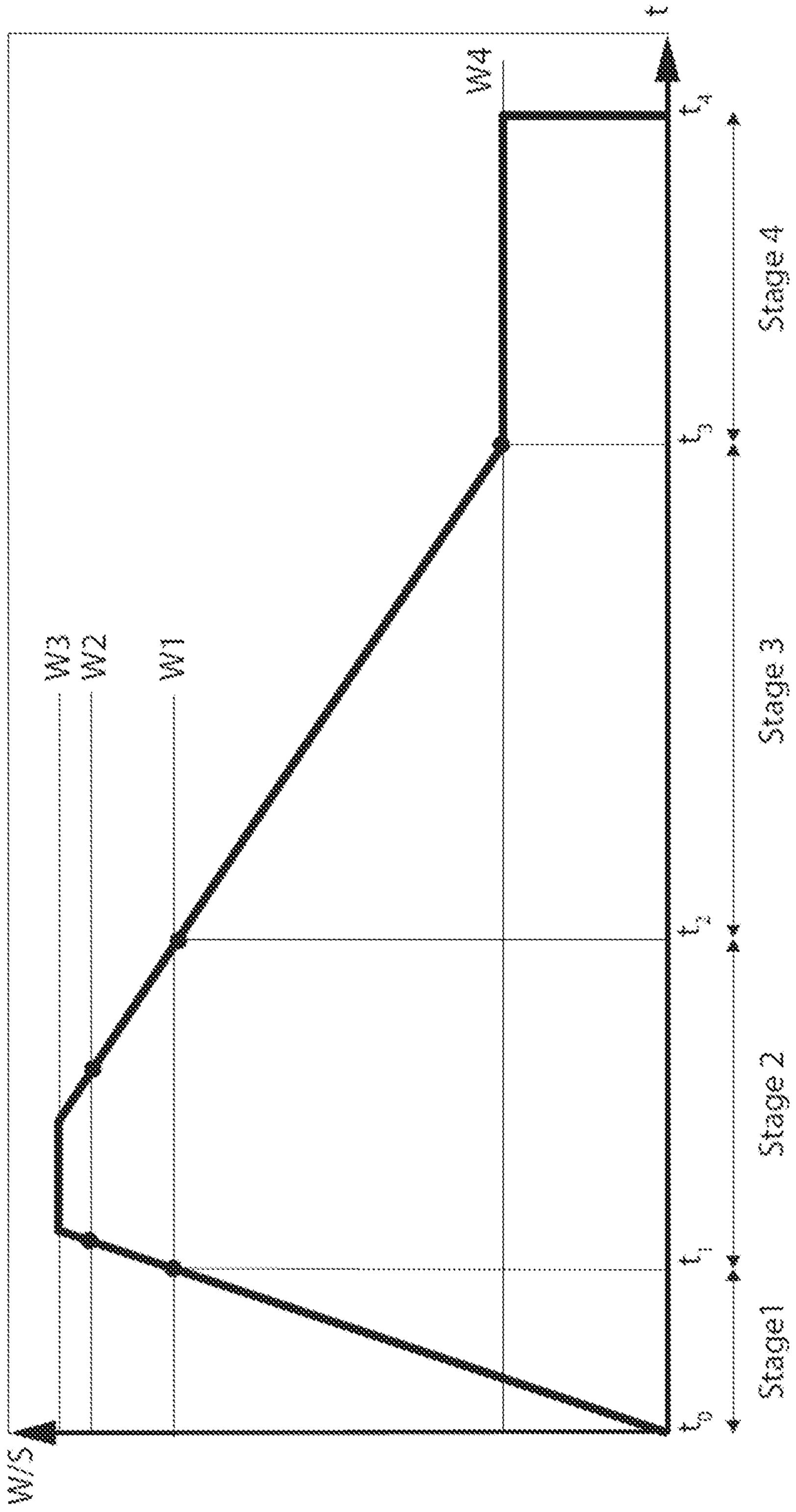
FIG. 2 illustrates a preferred energy density diagram to form a coating embodying the invention.

FIG. 2 illustrates a preferred energy density diagram to form a coating embodying the invention. Diagram presents 4 stages of the coating forming process.

Stage 1 is a pre-discharge stage characterised by ramping up process energy from zero up to a discharge threshold level W1 at which first microarc discharge appears on the surface. During this phase a ceramic coating begins to form on the metal body, as the metal of the metal body is oxidised. Zirconium oxide in monoclinic phase is formed from the zirconium in the electrolyte and consolidated into the ceramic layer.

At stage 2 the energy density is increased above discharge threshold W1 value and the process can be classified as plasma electrolytic oxidation (PEO) or micro arc oxidation (MAO). PEO mode forms rough surface of ceramic coating due to multiple discharge events. Roughness can be controlled through control of applied energy and duration of PEO stage.

Further increase of energy density during second stage 2 enables to reach level W2 at which formed zirconium oxide phase starts to transform from monoclinic to orthorhombic phase. That transformation starts at energy densities exceeding 20 kW/$dm^2$.

After reaching maximum process value of energy density W3 the process energy is made to reduce to a discharge threshold level W1 until the discharge effect disappears.

Stage 3 is a post-discharge oxidation during which process energy is gradually decreased until quasi stationary level W4. Absence of discharge allows to form more compact oxide ceramic which is positioned underneath porous top layer built during PEO stage.

Stage 4 of the process is characterised by maintaining energy density at relatively low level W4. During stage 4 the barrier layer on the interface with metal is formed.

Figure 3:
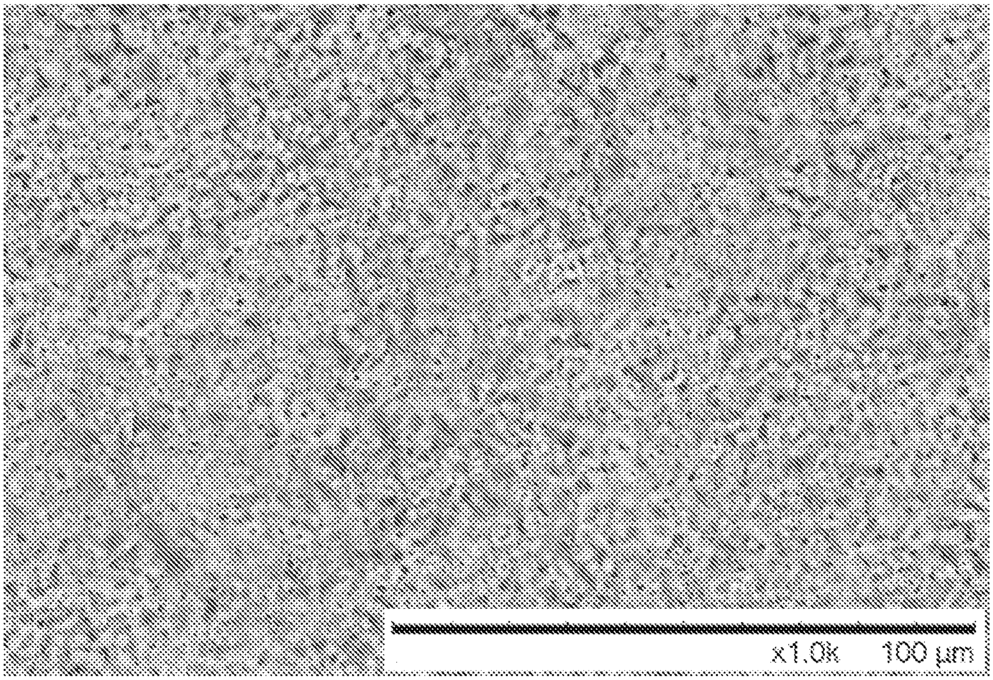
FIG. 3 is a scanning electron micrograph of a nanoceramic coating surface on titanium grade 5 alloy.

FIG. 3 is a scanning electron micrograph of a nanoceramic coating surface on titanium Grade 5 alloy. It demonstrates a highly developed surface with micro and nano roughness pattern. The mean roughness value is 0.8 micrometres. The pore size ranges from 0.1 to 2 micrometres. Achieved roughness and presence of nano- and micro pores are beneficial for osseointegration (Le Guehennec et al, Surface treatments of titanium dental implants for rapid osseointegration, Dental materials 23 (2007) 844-854).

Figure 4:
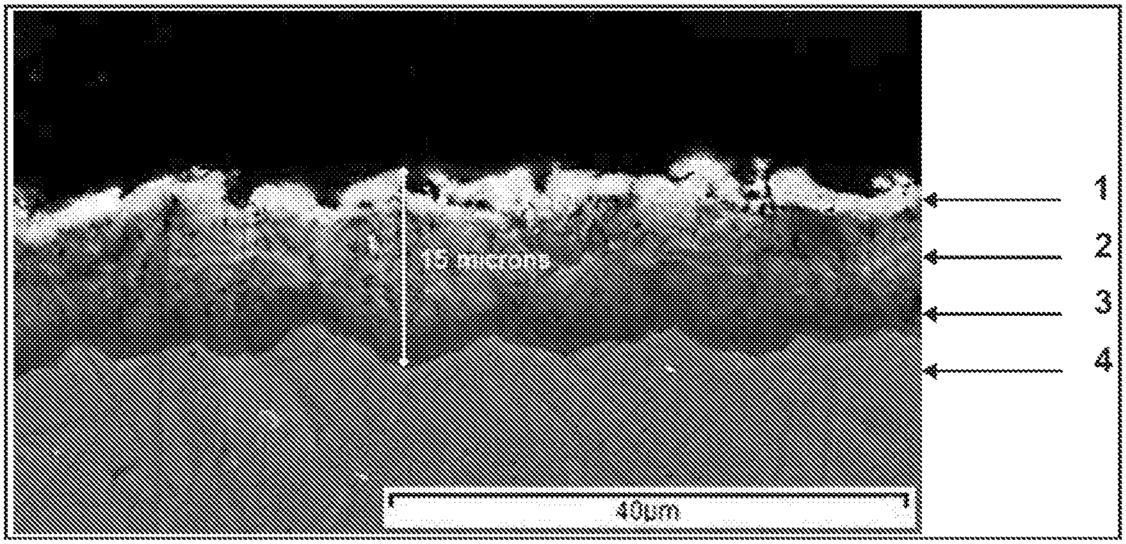
FIG. 4 is a scanning electron micrograph of a cross-section of nanoceramic coating on titanium grade 5 alloy.

FIG. 4 illustrates typical 3 layer structure of nanoceramic coating formed on titanium grade 5 alloy by invented multi stage electrochemical oxidation method. The mean average total thickness of ceramic layer is 13 micrometres. The top layer 1 has the mean average thickness of 3 micrometres, highly developed surface and average roughness of 0.8 micrometres. The middle layer 2 has the mean average thickness of 6 microns and is more compact and dense than the top layer 1. The bottom layer 3 has the mean average thickness of 4 micrometres. It has a very low porosity and serves as a barrier against migration of ions from substrate material 4.

Figure 5:
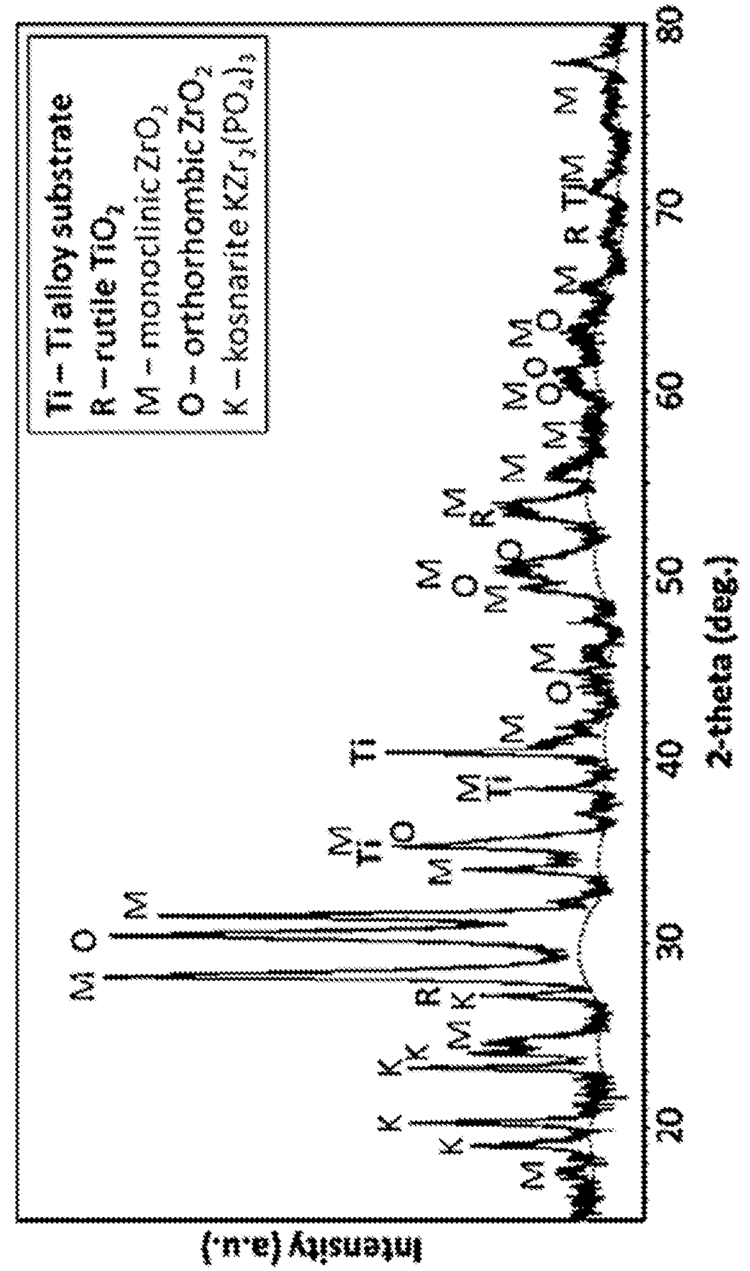
FIG. 5 is an X-ray diffraction (XRD) pattern of a nanoceramic coating on titanium grade 5 alloy.

FIG. 5 is an XRD pattern of a nanoceramic coating on titanium grade 5 alloy. It demonstrates the presence of zirconia and crystalline zirconium potassium phosphate of kosnarite type ($KZr_2$ $(PO_4)_3$). Zirconia is present in two crystalline forms: monoclinic and orthorhombic.

Figure 6:
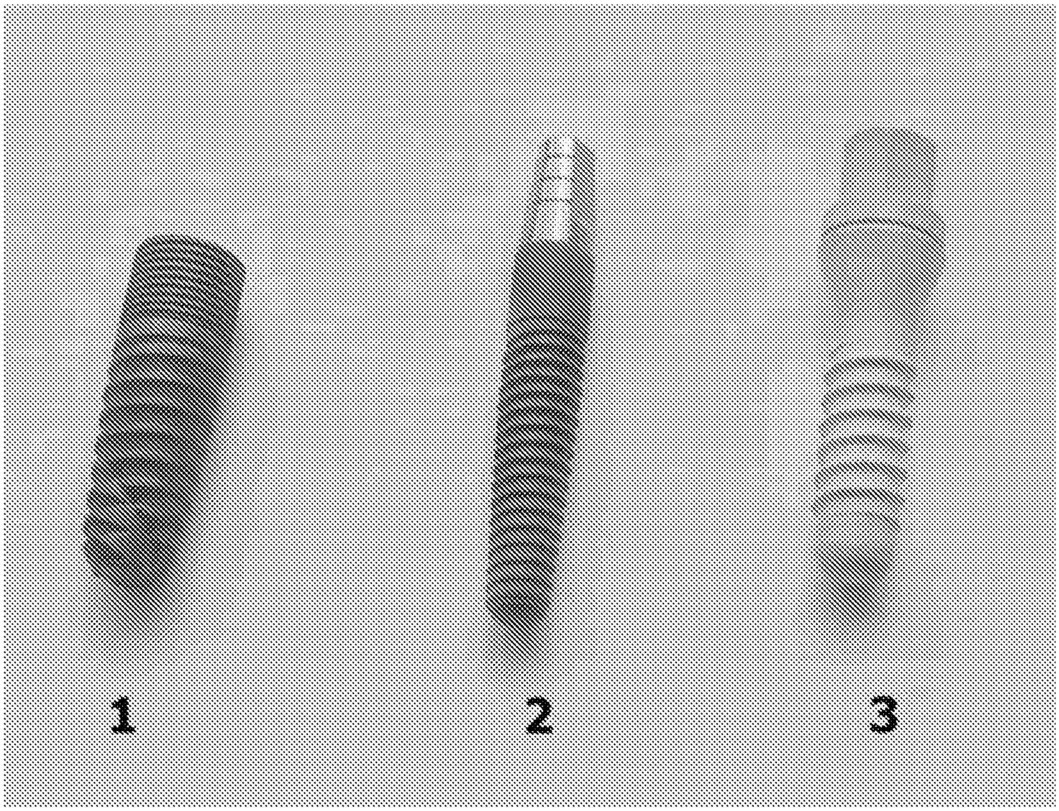
FIG. 6 is a photographic image of three titanium Grade 5 dental implants: 1—with etched surface; 2—with anodised surface; 3—with nanoceramic coating embodying the invention.

FIG. 6 is a photographic image of three dental implants made of Ti-6Al-4V titanium grade 5 alloy: 1—with etched surface; 2—with anodised surface; 3—with nanoceramic coating embodying the invention. FIG. 6 demonstrates that implant 1 with etched surface has a dark grey metallic colour. Anodising of that grade titanium does not improve the colour due to the presence of vanadium oxide in the anodic layer. Sample 5 has a nanoceramic coating made according to this invention and it has a bone-like colour which is distinctly different from the colour of implants 1 and 2.

Example 1

Dental implant was made of titanium grade 5 alloy (Ti-6Al-4V) rod by turning. The surface was subsequently etched in a solution of hydrofluoric acid HF and hydrochloric HCl acid. Electrochemical oxidation was conducted in an electrolytic apparatus as described above and illustrated in FIG. 1. Total coated implant surface area was 0.06 $dm^2$. The apparatus comprised a tank containing an electrolyte, and the implant and an electrode were coupled to a pulse power supply as illustrated in FIG. 1. The substrate and the electrode were arranged in contact with the electrolyte. The electrolyte was an aqueous solution containing 1.5 g/L of zirconium sulphate $Zr(SO_4)_2$, 2 g/L potassium pyrophosphate $K_4P_2O_7$, 0.4 g/L potassium hydroxide KOH and 2 g/L zirconium oxide $ZrO_2$ nano-powder, forming a stabilised colloidal solution.

The Pulse Generator applied a sequence of electrical pulses of alternating polarity between the substrate and the electrode. Pulse repetition frequency was 3 kHz. Pulse voltage amplitude was controlled in way that process energy density followed 4 stage mode required for forming 3 layer structure of ceramic coating as illustrated in FIG. 2.

At stage 1 energy density was increased from zero value to a discharge threshold level W1 equal to 12 kW/$dm^2$ at which first microarc discharge appears on the surface. Duration of Stage 1 was 2 min.

At stage 2 of plasma electrolytic oxidation the energy density is increased above level W2 equal to 20 kW/$dm^2$ at which formed zirconium oxide starts to transform from monoclinic to orthorhombic phase. PEO mode stage formed rough surface of ceramic coating due to multiple discharge events. After reaching the maximum process value of energy density W3 equal to 27 kW/$dm^2$ the process energy was made to reduce to a discharge threshold level W1 until the discharge effect disappeared. Duration of stage 2 was 6 min.

At stage 3 the process energy density was gradually decreased from W1 until quasi stationary level W4 equal to 4 kW/$dm^2$. The absence of discharge allowed to form compact oxide ceramic layer positioned underneath the porous top layer built during the PEO stage. Duration of stage 3 was 8 min.

At stage 4 the energy density was maintained at level W4. During stage 4 the barrier layer at the interface with metal was formed. Duration of stage 4 was 3 min.

Total duration of electrochemical oxidation was 19 min.

After electrochemical oxidation the implant was rinsed with deionised water in an ultrasonic tank for 20 minutes and then dried.

Scanning electron micrograph of the formed ceramic surface is illustrated in FIG. 3. The SEM image demonstrates a highly developed surface with micro- and nano-roughness pattern. The mean roughness value was 0.8 micrometres as measured by Veeco Dektak 150 Surface Profiler. The same profilometer was used for measuring surface roughness other provided examples as well. The pore size ranged from 0.1 to 2 micrometres.

A cross-section of the formed ceramic layer is presented in FIG. 4. SEM image demonstrates a three-layer structure of nanoceramic coating. The total average thickness of the ceramic layer is 15 micrometres. The top layer 1 has the mean average thickness of 4 micrometres, a highly developed surface and the mean average roughness Ra of 0.8 micrometres and porosity of 32%. The intermediate layer 2 has the mean average thickness of 8 microns and porosity of 9%. It is more compact than the top layer. The bottom layer 3 has the mean average thickness of 3 micrometres and porosity of just 2%. Due to a very low porosity it serves as a barrier against ion migration.

XRD pattern of the nanoceramic coating is presented in FIG. 5. The XRD demonstrates the presence of titania $TiO_2$ in a crystalline form of rutile; zirconia $ZrO_2$ and crystalline zirconium potassium phosphate of kosnarite type ($KZr_2$ $(PO_4)_3$). Zirconia was presented in two crystalline forms: monoclinic and orthorhombic. Comparison of the intensities of two crystalline phases of zirconia shows that the monoclinic phase is the major component. The average crystalline size was calculated on the base of the XRD data according to the Scherrer equation (B. D. Cullity & S. R. Stock, *Elements of X-Ray Diffraction*, 3rd Ed., Prentice-Hall Inc., 2001, p 167-171) Produced coating had the mean crystalline size of 50 nm.

Scratch resistance of the coating was evaluated by VTT scratch tester with diamond indenter with increasing load over 15 mm distance. Indenter reached the substrate at critical load of 15 N which is a higher value compared to measured anodic oxide films (5-8N) or galvanically deposited HA (4-7N). Around 80% of the distance before the perforation the indenter ploughs through the middle layer 2 which constitutes only 50% of the coating thickness (FIG. 4). That demonstrated that a high scratch resistance of the coating is provided predominantly by the intermediate layer of ceramic material.

Produced coating has a bone like colour demonstrated in FIG. 6 which is a photographic image of three dental implants made of Ti-6Al-4V titanium grade 5 alloy: 1—with etched surface; 2—with anodised surface; 3—with ceramic coating described in this example. FIG. 6 demonstrates that implant 1 with etched surface has dark grey metallic colour. Anodising of that grade titanium does not improve the colour due to the presence of vanadium oxide in the anodic oxide layer. Implant 3 has a nanoceramic coating made according to this invention and it has a bone-like colour which is distinctly different from the colour of implants 1 and 2. Colour of ceramic surface evaluated by Datacolor 660 spectroscope provided values in CIELAB colour space corresponding to L*=70, a*=+0.3 and b*=+4. The low values of a* and b* indicated a well balanced combination between red-green and yellow-blue colours, whereas high values of lightness L* indicate a close to white light-grey shade of the surface. Optical reflectance (%) was measured by a spectrophotometer CM 2600 (Konica Minolta) in the visible wavelength range. Reflectance of teeth according to VITA Zahnfabric ranges in the interval between 30% and 70%. Mean reflectance values for non-coated Ti alloy implants with etched surface and anodised implants laid in the range of 22%-28% across visible light spectrum while produced implant with ceramic coating demonstrated surface reflectance in the range 35%-37%.

Example 2

Magnesium alloy AZ71 was used for making a biodegradable bone implant. The implant was manufactured by die casting and cleaned in alkaline bath. Ceramic coating was applied in order to provide slower implant weight loss and reduction in Mg alloy ion release in the blood plasma.

Electrochemical oxidation was conducted in an electrolytic apparatus as described above and illustrated in FIG. 1.

The electrolyte was an aqueous solution containing 2 g/L sodium fluoride, 2.5 g/L zirconium sulphate $Zr(SO_4)_2$, 3 g/L potassium pyrophosphate $K_4P_2O_7$, 2.5 g/L potassium hydroxide KOH.

The 4 stage oxidation process lasted 14 min and it included stage one of 1 min duration, stage 2 of 4 min, stage 3 of 6 min and stage 4 of 3 min.

Formed coating contained oxides of magnesium MgO and zirconium $ZrO_2$ and crystalline zirconium potassium phosphate of kosnarite type $KZr_2(PO_4)_3$.

Formed coating had average thickness of 8 micrometres and roughness Ra=1.2 micrometres.

Example 3

Pure tantalum Ta was used for making a porous intraosseous implant by additive manufacturing technique of 3D printing. After manufacturing, the implant was etched in a solution of nitric $HNO_3$ and hydrochloric HCl acids.

Electrochemical oxidation was conducted in an electrolytic apparatus as described above and illustrated in FIG. 1.

The electrolyte was an aqueous solution containing 2 g/L of zirconium sulphate $Zr(SO_4)_2$, 2 g/L sodium pyrophosphate $Na_4P_2O_7$, 0.5 g/L sodium hydroxide NaOH, 0.1 g/L silver sulphate and 3 g/L hydroxyapatite HA nano-powder, forming a stabilised colloidal solution.

The 4 stage oxidation process lasted 26 min and it included stage one of 3 min duration, stage 2 of 8 min, stage 3 of 12 min and stage 4 of 3 min.

Formed coating contained tantalum pentoxide $Ta_2O_5$, zirconia $ZrO_2$ and hydroxyapatite. Sodium zirconium phosphate $NaZr_2P_3O_{12}$ and silver sodium zirconium phosphate $AgNaO_8P_2Zr$ are present in the coating. Formed coating had average thickness of 16 micrometres and roughness Ra=0.7 micrometres.

Example 4

Titanium beta alloy Ti-15Nb-8Zr (ZN1) produced by UJP PRAHA a.s. was used to manufacture dental implant prototype. Alloy was by made by vacuum arc melting with subsequent re-melting to ensure chemical homogeneity. It contained crica 15% of niobium and 8% of zirconium.

Dental implant prototype was manufactured by CNC machining.

After manufacturing implant was etched in a solution of nitric $HNO_3$ and hydrochloric HCl acids.

Electrochemical oxidation was conducted in an electrolytic apparatus as described above and illustrated in FIG. 1.

The electrolyte was an aqueous solution containing 1 g/L of zirconium fluoride $ZrF_4$, 12 g/L sodium pyrophosphate $Na_4P_2O_7$, 1 g/L zirconium oxide $ZrO_2$ nano-powder, forming a stabilised colloidal solution.

The 4 stage oxidation process lasted 16 min and it included stage one of 1 min duration, stage 2 of 8 min, stage 3 of 7 min and stage 4 of 2 min.

Formed coating contained titanium oxide $TiO_2$ in a crystalline form of rutile and sodium titanium phosphate $NaTi_2(PO_4)_3$; zirconia $ZrO_2$ and zirconium potassium phosphate of kosnarite type ($KZr_2(PO_4)_3$). Zirconia was presented in two crystalline forms: monoclinic and orthorhombic.

Formed coating had the mean average thickness of 20 micrometres and roughness Ra=1.1 micrometres.

Scratch resistance of the coating evaluated by VTT scratch tester with diamond indenter demonstrated a critical load of 17 N.

Colour of produced ceramic surface provided values in CIELAB colour space corresponding to L*=76, a*=−0.2 and b*=+3. The low values of a* and b* indicated a well balanced combination between red-green and yellow-blue colours, whereas high values of lightness L* indicated a close to white light-grey shade of the surface. Optical reflectance measured in the visible wavelength range lied in the range of 38%-42%.

The invention claimed is:

1. An implant comprising:

a metal body having a ceramic coating, in which the ceramic coating material contains monoclinic and orthorhombic phases of zirconium oxide $ZrO_2$, and at least one Group I-IV multi-metal phosphate, and the ceramic coating having a nano-crystalline structure with an average grain size of between 20 and 100 nanometres.

2. An implant according to claim 1, in which the ceramic coating is formed by electrochemical oxidation of a portion of the surface of the metal body.

3. An implant according to claim 1, in which the ceramic coating material contains at least four elements selected from the group consisting of: zirconium, titanium, magnesium, oxygen, phosphorus, calcium, fluoride, potassium, sodium, strontium, sulphur, argentum, zinc, copper, silicon, and gallium.

4. An implant according to claim 1, in which the at least one Group I-IV multi-metal phosphate comprises an alkali-metal phosphate.

5. An implant according to claim 4, in which the ceramic coating material comprises potassium zirconium phosphate of kosnarite $KZr_2$ $(PO_4)_3$, sodium zirconium phosphate $NaZr_2(PO_4)_3$, or silver sodium zirconium phosphate $AgNaO_8P_2Zr$.

6. An implant according to claim 4, in which the ceramic coating material comprises sodium titanium phosphate $NaTi_2(PO_4)_3$ or potassium titanyl phosphate $KTiOPO_4$.

7. An implant according to claim 1, in which the metal body is selected from the group consisting of titanium, zirconium, magnesium, tantalum or an alloy or intermetallic of any of these metals.

8. An implant according to claim 1, in which the ceramic surface has a roughness Ra of greater than or equal to 0.4 μm, or 0.5 μm, or 0.6 μm, and less than or equal to 1.2 μm, or 1.5 μm, or 2 μm.

9. An implant according to claim 1, in which the ceramic coating has a thickness of between 5 micrometres and 40 micrometres.

10. An implant according to claim 1, in which the ceramic coating is impregnated or top coated with one or more of an anti-inflammatory drug, a bone stimulating material, a bone healing enhancement drug, or a cancer treatment material.

11. An implant according to claim 1, in which the ceramic coating comprises:

a top surface layer, an intermediate layer, and a barrier layer at an interface with the metal body, optionally in which the surface layer of the ceramic coating has a bone-like colour with CIELAB colour space values of L* from 65 to 80, a* from −3 to +3 and b*from −2 to +5 and reflectance in the visible wavelength range above 30%.

12. An implant according to claim 11, in which the intermediate layer of the ceramic coating is a scratch-resistant layer, and/or in which the intermediate layer of the ceramic coating has a porosity of between 5% and 15%, and/or in which the barrier layer of the ceramic coating has a porosity below 5%.

13. A method of forming an implant comprising a metal body having a ceramic coating, comprising:

electrochemical oxidation of at least a portion of the surface of a metal body in aqueous electrolyte, in which the metal body and/or the electrolyte contains zirconium, and in which the electrolyte contains phosphorus and at least one of sodium or potassium, such that the electrochemical oxidation forms a ceramic coating on the metal body, the ceramic coating containing monoclinic and orthorhombic phases of zirconium oxide $ZrO_2$, and at least one I-IV multi-metal phosphate.

14. A method according to claim 13, in which the electrochemical oxidation process comprises the step of electrically biasing the metal body with respect to the electrolyte by applying a sequence of voltage pulses of alternating polarity.

15. A method according to claim 13, in which the electrolyte contains at least two elements from a group consisting of zirconium, titanium, magnesium, phosphorus, calcium, fluoride, potassium, sodium, strontium, sulphur, argentum, zinc, copper, silicon, and gallium.

16. A method according to claim 13, in which electrochemical oxidation is conducted in a plasma discharge (PEO) mode for at least one interval of time, and non-discharge modes for at least two intervals of time, and/or in which the energy density of the electrochemical oxidation process exceeds 20 $kW/dm^2$.

17. A method according to claim 13, in which the process of electrochemical oxidation comprises the following consecutive steps:

a) pre-discharge energy ramping step, b) plasma electrolytic oxidation step in which the process energy density exceeds the value of 20 $kW/dm^2$, c) post-discharge energy decrease step, optionally comprising the additional step of:

d) low energy quasi stationary step in which the process energy density does not exceed the value of 5 $kW/dm^2$.

18. A method according to claim 13, in which the implant is an implant according to claim 1.

19. A method according to claim 13, comprising the step of manufacturing of the metal body by at least one method from a group comprising forging, casting, thixomolding, machining, turning, milling, additive manufacturing or chemical vapour deposition, wire erosion and spark erosion, and/or comprising the step, before electrochemical oxidation, of surface preparation of the metal body by at least one method from a group comprising polishing, blasting, etching or cleaning.

20. An implant according to claim 1, in which the at least one Group I-IV multi-metal phosphate comprises an alkali-metal zirconium phosphate, or an alkali-metal titanium phosphate.

21. An implant according to claim 11, in which the surface layer of the ceramic coating has a porosity of greater than 25%.

* * * * *